United States Patent [19]

Ingram et al.

[11] Patent Number: 5,632,988
[45] Date of Patent: May 27, 1997

[54] POLYPEPTIDE INHIBITORS OF GAMMA INTERFERON

[75] Inventors: Richard Ingram, Scotch Plains; Hung V. Le, Rockaway; Lata Ramanathan, West Orange, all of N.J.

[73] Assignee: Schering Corporation, Kenilworth, N.J.

[21] Appl. No.: 859,292

[22] PCT Filed: Oct. 19, 1990

[86] PCT No.: PCT/US90/05908

§ 371 Date: Apr. 7, 1992

§ 102(e) Date: Apr. 7, 1992

Related U.S. Application Data

[63] Continuation-in-part of Ser. No. 425,543, Oct. 23, 1989, abandoned.

[51] Int. Cl.$^6$ .......................... A61K 39/00; A61K 38/00; C07K 5/00; C07K 16/00
[52] U.S. Cl. ................. 424/185.1; 530/300; 530/326; 530/327; 530/328; 530/330; 514/2; 514/14
[58] Field of Search .................. 530/326, 327, 530/328, 330, 300; 514/2, 14; 424/185.1

[56] References Cited

U.S. PATENT DOCUMENTS

| | | | |
|---|---|---|---|
| 3,927,204 | 12/1975 | Neri et al. | 514/2 |
| 4,597,967 | 7/1986 | Beachey | 514/2 |
| 4,897,264 | 1/1990 | Novick et al. | 424/85.5 |
| 5,087,616 | 2/1992 | Myers et al. | 514/2 |

FOREIGN PATENT DOCUMENTS 9109127   6/1991   WIPO .

OTHER PUBLICATIONS

Guari–Bitman, FEBS letters 148 (1):17–20, 1982.
Bermon et al, Exp. Cell. Res. 183:215–228. 1989.
Frohman et al, PNAS 85:1292–1296. 1988.
Koide et al, PNAS 85:3120–3124. 1988.
Aquet et al, Cell 55:273, 1988.
Calderon et al, PNAS 85:4837, 1988.
Foster et al, Biophys J. 53:182a. 1988(abstract).
Guerriero et al, Biochemistry 25:8372. 1986.
Kemp et al, J. Biol. Chem. 262:2542. 1987.
Langer et al, Immunology Today 9:393. 1988.
Lukas et al, Biochemistry 25:1458. 1986.
Reynolds, "Martindile The Extra Pharmacopoeia" The Pharmaceutical Press, London 1982. pp. 390–391.
Foster et al, Arch. Biochem. Biophys. 280(2):397–404. 1990.
Koide et al. 1988. Calcium influx and the $Ca^{2+}$–calmodulin complex . . . PNAS USA 85: 3120–3124.
Guerriero et al. 1986. Domain Organization of Chicken Gizzard Myosin . . . Biochemistry 25: 8372–81.
Kemp et al. 1987. The Calmodulin Binding Domain of Chicken Smooth . . . JBC. 262 (6): 2542–2548.
Aquet et al. 1988. Molecular Cloning and Expression of the Human Interferon-γ Receptor Cell 55:273–280.
Langer et al. 1988. Interferon Receptors. Immunol. Today 9 (12): 393–400.

*Primary Examiner*—James C. Housel
*Assistant Examiner*—N. M. Minnifield
*Attorney, Agent, or Firm*—Paul G. Lunn; Norman C. Dulak

[57] ABSTRACT

Novel synthetic polypeptides comprising the amino acid subsequence Arg-Arg-Lys-Trp-Gln are provided by this invention. Also provided are methods for the use of such polypeptides, other known polypeptides containing such subsequence and a variety of acidic or basic polypeptides and proteins as inhibitors of the binding of gamma interferon to its cellular receptors. The methods of this invention are potentially applicable to the treatment of pathological conditions believed to be mediated by gamma interferon, such as autoimmune disease.

4 Claims, 4 Drawing Sheets

POLYPEPTIDE INHIBITORS OF GAMMA INTERFERON

BACKGROUND OF THE INVENTION

The present application is the United States national application corresponding to International Application No. PCT /US90/05908, filed Oct. 19, 1990 and designating the United States, which PCT application is in turn a continuation-in-part of U.S. application Ser. No. 07/425, 543, filed Oct. 23, 1989 now abandoned, the benefit of which applications is claimed pursuant to the provisions of 35 U.S.C. §§129,363, and 365(C).

Gamma interferon is a cytokine produced by activated helper T cells, one of the most characteristic activities of which is the upregulation of MHC class II gene expression in macrophages, mature B cells and T cells. The expression of class II antigens is a hallmark of antigen-presenting cells. Gamma interferon is also known to upregulate the expression of class II antigens in cells that are not primary antigen-presenting cells, such as epithelial cells, fibroblasts, astrocytes, endothelial cells and smooth muscle cells. The upregulation of class II antigens in these cell types is often correlated with the development of autoimmune disease.

Although the mechanism by which gamma interferon exerts its effects on cells is not understood, it is known that it binds to specific cellular receptors [Langer et al., Immunology Today 9:393 (1988)]. Aguet et al. [Cell 55:273 (1988)] have cloned and sequenced a gene for a gamma interferon receptor. The molecular weight of the encoded protein deduced from the sequence is consistent with the molecular weight of a gamma interferon receptor recently isolated from human placenta [Calderon et al., Proc. Natl. Acad. Sci. USA 85:4837 (1988)].

Because gamma interferon acts at specific cellular receptors and is implicated in autoimmune disease, agents which could inhibit the binding of such interferon to its cellular receptors might be useful therapeutically.

SUMMARY OF THE INVENTION

This invention provides novel polypeptides containing the amino acid subsequence Arg-Arg-Lys-Trp-Gln. More particularly, this invention provides novel polypeptides selected from the group consisting of:

Arg-Arg-Lys-Trp-Gln,

Lys-Lys-Tyr-Met-Ala-Arg-Arg-Lys-Trp-Gln,

Arg-Met-Lys-Lys-Tyr-Met-Ala-Arg-Arg-Lys-Trp-Gln, and

Lys-Lys-Tyr-Met-Ala-Arg-Arg-Lys-Trp-Gln-Lys-Thr-Gly-His-Ala-Val.

The present invention further provides methods for inhibiting the binding of gamma interferon to cellular receptors, comprising contacting cells bearing receptors for gamma interferon with an effective amount of a polypeptide or protein selected from the group consisting of:

(a) a protamine or a salt thereof;

(b) a polypeptide comprising polylysine, polyarginine or a mixture of such residues;

(c) a polypeptide comprising polyglutamic acid, polyaspartic acid or a mixture of such residues; and (d) a polypeptide comprising the amino acid subsequence Arg-Arg-Lys-Trp-Gln and from 5 to about 30 amino acid residues, which polypeptide or protein has a Ki of about 25 μM or less in inhibiting the specific binding of $^{125}$I-recombinant human gamma interferon to Daudi cells at 4° C.

Because the polypeptides and proteins of the invention inhibit the binding of gamma interferon to its cellular receptors, they also inhibit the biological effects of such interferon such as antiviral effects and the induction of class II major histocompatibility antigens.

This invention thus also provides methods for inhibiting antiviral effects of gamma interferon, comprising contacting cells capable of responding to gamma interferon by producing an antiviral response with an effective amount of a polypeptide or protein selected from the group consisting of:

(a) a protamine or a salt thereof;

(b) a polypeptide comprising polylysine, polyarginine or a mixture of such residues;

(c) a polypeptide comprising polyglutamic acid, polyaspartic acid or a mixture of such residues; and (d) a polypeptide comprising the amino acid subsequence Arg-Arg-Lys-Trp-Gln and from 5 to about 30 amino acid residues.

This invention still further provides methods for inhibiting gamma interferon-induced expression of class II major histocompatibility antigens, comprising contacting cells capable of responding to gamma interferon by induction of expression of class II major histocompatibility antigens with an effective amount of a polypeptide or protein selected from the group consisting of:

(a) a protamine or a salt thereof;

(b) a polypeptide comprising polylysine, polyarginine or a mixture of such residues;

(c) a polypeptide comprising polyglutamic acid, polyaspartic acid or a mixture of such residues; and (d) a polypeptide comprising the amino acid subsequence Arg-Arg-Lys-Trp-Gln and from 5 to about 30 amino acid residues.

The polypeptides and methods of the present invention are useful for the in vitro study of the mechanism of gamma interferon binding to various cell types and for screening for agonists or other antagonists of such binding. They also have potential utility for the treatment of pathological conditions such as autoimmune disease, which are believed to be mediated by gamma interferon.

BRIEF DESCRIPTION OF THE FIGURES

This invention can be more readily understood by reference to the accompanying figures, in which:

FIG. 1 is a graphical representation of the inhibition by poly(D-lysine) (open squares) and poly(L-lysine) (closed squares) of the binding of 125I-recombinant human gamma interferon to Daudi cells. Percent specifically bound radioactivity is shown as a function of polypeptide concentration.

FIG. 2 is a graphical representation of the inhibition by poly(L-glutamic acid) of the binding of 1251I-recombinant human gamma interferon to Daudi cells, showing percent specifically bound radioactivity as a function of polypeptide concentration.

FIG. 3 is a graphical representation of the inhibition by salmon protamine sulfate of the binding of 1251I-recombinant human gamma interferon to Daudi cells, showing percent specifically bound radioactivity as a function of protamine sulfate concentration.

FIG. 4 is a graphical representation of the inhibition by a synthetic polypeptide of the binding of 1251-recombinant human gamma interferon to Daudi cells, showing percent specifically bound radioactivity as a function of polypeptide concentration. The polypeptide had the amino acid sequence Ala-Lys-Lys-Leu-Ser-Lys-Asp-Arg-Met-Lys-Lys-Tyr-Met-Ala-Arg-Arg-Lys-Trp-Gln-Lys

DESCRIPTION OF THE INVENTION

All references cited herein are hereby incorporated in their entirety by reference. All amino acid sequences disclosed follow the normal convention, with the amino terminus on the left and the carboxyl terminus on the right.

In the course of a search for specific inhibitors of recombinant human gamma interferon, it has surprisingly been found that a number of polypeptides and proteins are potent inhibitors of the binding of gamma interferon to its cellular receptors. The antagonistic actions of these polypeptides and proteins have been demonstrated in a radioligand-receptor assay system employing the polypeptides and proteins of the invention, 125I-recombinant human gamma interferon, and cells bearing specific receptors for such interferon.

This inhibition of interferon binding is specific; the same polypeptides and proteins did not inhibit the binding of human granulocyte/macrophage colony stimulating factor (GM-CSF) or interleukin-4 to their receptors in radioligand-receptor assay systems.

Gamma interferon possesses antiviral activity (i.e., it protects cells from virally-induced cytopathic effects). It also is a potent inducer of the maturational differentiation of pro-monocytes to premacrophages. The antiviral activity of gamma interferon can be demonstrated in an assay system in which cultured human diploid foreskin cells are infected with murine encephalomyocarditis virus to produce measurable cytopathic effects [Rubinstein et al., J. Virol. 37:755 (1981)]. The differentiation-inducing activity of gamma interferon can be demonstrated in an assay in which the interferon induces the surface expression of framework antigens (HLA-DR) of the human histocompatibility complex in a promonocytic cell line [Kelley et al., J. Immunol. 132:240 (1984)].

The polypeptides and proteins of the present invention were completely inactive in both of these assay systems, at concentrations at which they produced strong inhibition of the binding of 125I-recombinant human gamma interferon to cellular receptors in the radioreceptor binding assay described below.

The present invention encompasses three principal categories of gamma interferon inhibitors: (1) protamines and salts thereof, (2) highly charged homo- or heteropolypeptides containing lysine and/or arginine or glutamic acid and/or aspartic acid and (3) polypeptides comprising the amino acid subsequence Arg-Arg-Lys-Trp-Gln.

Protamines are strongly basic proteins of relatively low molecular weight which are associated with nucleic acids and can be obtained in large quantities from ripe sperm cells of fish. Some examples of protamines are salmine from salmon, clupeine from herring, and sturine from sturgeon sperm. Although salmine has been used below for purposes of illustration, all protamines can be used in the methods of this invention.

The protamines are available commercially or can readily be prepared using known methods. Salmine can be purchased, e.g., from Sigma Chemical Co., St. Louis, Mo. Because of their highly basic character, protamines are frequently provided as chloride, phosphate, sulfate or other salts. Protamine sulfate was used in an example below.

The second category of inhibitors is exemplified below by poly(D-lysine), poly(L-lysine) and poly(L-glutamic acid). Although homopolymers were used for illustration purposes, heteropolymers containing both lysine and arginine or both glutamic acid and aspartic acid, in random or predetermined order, can be used as well. Both D and L isomers of the amino acid residues can be used, or mixtures of the two. Size is not critical. Polypeptides ranging from about 3,863 to about 66,000 daltons are illustrated below, but acidic or basic polypeptides of from about 3,000 to about 100,000 daltons or more can be used.

A wide variety of homo- and heteropolypeptides are available commercially from sources such as Sigma Chemical Co., St. Louis, Mo. Alternatively, they can be synthesized using standard methods and fractionated by size using gel filtration or other methods.

The third category of inhibitors was unexpectedly discovered during investigations of polypeptides, the amino acid sequences of which corresponded to subsequences of the calmodulin binding domain of chicken smooth muscle myosin light-chain kinase (MLCK) [Kemp etal., J. Biol. Chem. 262:2542 (1987)]. It must be understood, however, that it is the Arg-Arg-Lys-Trp-Gln subsequence within these polypeptides that is crucial to this invention. Residues corresponding to other residues of MLCK are not essential.

As shown below, replacement of the amino-terminal arginine residue of the subsequence by a lysine residue markedly reduced the inhibitory capability of a polypeptide containing the subsequence. Similar adverse effects were observed when the glutamine residue was replaced by an alanine residue or the tryptophan residue was replaced by an alanine residue, in other polypeptides.

Any polypeptide containing the Arg-Arg-Lys-Trp-Gln subsequence can be used in this invention, as long as it has a Ki of about 25 µM or less in inhibiting the specific binding of 125I-recombinant human gamma interferon to Daudi cells at 4° C. The polypeptides can contain from 5 to about 30 amino acid residues. Larger polypeptides are also contemplated by this invention, as long as they meet the functional Ki limitation.

It must be stressed that the polypeptides of the invention will bind to any cells which have gamma interferon receptors, such as B cells, T cells, eosinophiles, smooth muscle cells, promyelocytes, macrophages, erythroid cells, monocytes and granulocytes. Daudi cells are merely a convenient, readily available cell line which can be used to quickly determine whether a given polypeptide has an adequate Ki value. Other cell lines can also be used to make this determination. For example, essentially the same Ki values have been obtained using the U-937 human histiocytic lymphoma line (ATCC CRL 1593).

The polypeptides are synthesized by a suitable method such as by exclusive solid phase synthesis, partial solid phase methods, fragment condensation or classical solution synthesis. The polypeptides are preferably prepared by solid phase peptide synthesis as described by Merdfield, J. Am. Chem. Soc. 85:2149 (1963). The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aromatic urethane type protecting groups [e.g., benzyloxycarbonyl (Cbz), substituted benzyloxycarbonyl and 9-fluorenylmethyloxycarbonyl (Fmoc)], aliphatic urethane protecting groups [e.g., t-butyloxycarbonyl (Boc), isopropyloxycarbonyl, cyclohexyloxycarbonyl] and alkyl type protecting groups (e.g., benzyl, triphenylmethyl). The preferred protecting group is Boc. The side-chain protecting groups for Tyr include tetrahydropyranyl, tert.-butyl, trityl, benzyl, Cbz, 4-Br-Cbz and 2,6-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group of Asp is cyclohexyl. The side-chain protecting groups for Thr and Ser include acetyl, benzoyl, trityl, tetrahydropyranyl, benzyl, 2,6-dichlorobenzyl and Cbz. The preferred protecting group for Thr and Ser is benzyl. The side-chain protecting groups for Arg include nitro, Tos, Cbz, adamantyloxycarbonyl and Boc. The preferred protecting group for Arg is Tos. The side-chain amino group of Lys may be protected with Cbz, 2-Cl-Cbz, Tos or Boc. The 2-Cl-Cbz group is the preferred protecting group for Lys.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide.

Solid phase synthesis is usually carded out from the carboxyl-terminus by coupling the alpha-amino protected (side-chain protected) amino acid to a suitable solid support. An ester linkage is formed when the attachment is made to a chloromethyl or hydroxymethyl resin, and the resulting polypeptide will have a free carboxyl group at the C-terminus. Alternatively, when a benzhydrylamine or p-methylbenzhydrylamine resin is used, an amide bond is formed and the resulting polypeptide will have a carboxamide group at the C-terminus. These resins are commercially available, and their preparation has been described by Stewart et al., "Solid Phase Peptide Synthesis" (2nd Edition), Pierce Chemical Co., Rockford, Ill., 1984.

The C-terminal amino acid, protected at the side-chain if necessary and at the alpha-amino group, is coupled to the benzhydrylamine resin using various activating agents including dicyclohexylcarbodiimide (DCC), N,N'-diisopropylcarbodiimide and carbonyldiimidazole. Following the attachment to the resin support, the alpha-amino protecting group is removed using trifluoroacetic acid (TFA) or HCl in dioxane at a temperature between 0° and 25° C. Dimethylsulfide is added to the TFA after the introduction of methionine (Met) to suppress possible S-alkylation. After removal of the alpha-amino protecting group, the remaining protected amino acids are coupled stepwise in the required order to obtain the desired sequence.

Various activating agents can be used for the coupling reactions including DCC, N,N'-diisopropylcarbodiimide, benzotriazol-1-yl-oxy-tris-(dimethylamino)-phosphonium hexafluorophosphate (BOP) and DCC-hydroxybenzotriazole (HOBt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction is monitored at each stage, e.g., by the ninhydrin reaction as described by Kaiser et al., Anal. Biochem. 34:595 (1970). In cases where incomplete coupling is found, the coupling reaction is repeated. The coupling reactions can be performed automatically with commercially available instruments.

After the entire assembly of the desired polypeptide, the polypeptide-resin is cleaved with a reagent such as liquid HF for 1–2 hours at 0° C., which cleaves the polypeptide from the resin and removes all side-chain protecting groups. A scavenger such as anisole is usually used with the liquid HF to prevent cations formed during the cleavage from alkylating the amino acid residues present in the polypeptide. The polypeptide-resin may be deprotected with TFA/dithioethane prior to cleavage if desired.

Side-chain to side-chain cyclization on the solid support requires the use of an orthogonal protection scheme which enables selective cleavage of the side-chain functions of acidic amino acids (e.g., Asp) and the basic amino acids (e.g., Lys). The 9-fluorenylmethyl (Fm) protecting group for the side-chain of Asp and the 9-fluorenylmethyloxycarbonyl (Fmoc) protecting group for the side-chain of Lys can be used for this purpose. In these cases, the side-chain protecting groups of the Boc-protected polypeptide-resin are selectively removed with piperidine in DMF. Cyclization is achieved on the solid support using various activating agents including DCC, DCC/HOBt or BOP. The HF reaction is carried out on the cyclized polypeptide-resin as described above.

Recombinant DNA methodology can also be used to prepare the polypeptides. The known genetic code, tailored if desired for more efficient expression in a given host organism, can be used to synthesize oligonucleotides encoding the desired amino acid sequences. The phosphoramidite solid support method of Matteucci et al. [J. Am. Chem. Soc. 103:3185 (1981)] or other known methods can be used for such synthesis. The resulting oligonucleotides can be inserted into an appropriate vector and expressed in a compatible host organism.

The polypeptides of the invention can be purified using HPLC, gel filtration, ion exchange and partition chromatography, countercurrent distribution or other known methods.

Whether a given polypeptide containing the Arg-Arg-Lys-Trp-Gln subsequence is encompassed by this invention can readily be determined by routine experimentation using the Daudi cell radioligand-receptor assay system described below. Recombinant human gamma interferon which can be used in this system is available commercially, e.g., from Genzyme Corp., Boston, Mass.. Such interferon can readily be labeled with iodine-125 using, e.g., the lactoperoxidase method [David et al., Biochemistry 13:1014 (1974)] or the method of Bolton et al. [Biochem. J. 133:529 (1973)].

Pharmaceutical compositions can be prepared which contain effective amounts of one or more of the polypeptides and proteins of the invention or pharmaceutically acceptable salts thereof and a physiologically acceptable carrier. Such carriers are well known to those skilled in the art. The polypeptides and proteins can be administered directly or in the form of a composition to a human patient afflicted, e.g., by autoimmune disease or another disease mediated by gamma interferon.

Determination of the proper dosage of a polypeptide or protein of the invention for a particular situation is within the skill of the art. Generally, treatment is initiated with smaller dosages that are less than optimum. Thereafter, the dosage is increased by small increments until the optimum effect under the circumstances is reached. For convenience, the total daily dosage may be divided and administered in portions during the day if desired.

The amount and frequency of administration of the polypeptides and proteins of the invention and the pharmaceutically acceptable salts thereof will be regulated according to the judgment of the attending clinician, taking into account such factors as age, condition and size of the patient and severity of the symptom(s) being treated.

EXAMPLES

Unless otherwise specified, percentages given below for solids in solid mixtures, liquids in liquids, and solids in liquids are on a wt/wt, vol/vol and wt/vol basis, respectively.

Sources of Polypeptides and Proteins

Poly(D-lysine), poly(L-lysine) and poly(L-glutamic acid) having molecular weights of about 12,946, 3,863 and 66,000 daltons, respectively, and salmine were purchased from Sigma Chemical Co., St. Louis, Mo.

The following synthetic polypeptides were produced by solid-phase automated peptide synthesis using an Applied Biosystems Model 430A synthesizer and standard automated solid-phase peptide synthetic techniques:

| | |
|---|---|
| Ala-Lys-Lys-Leu-Ser-Lys-Asp-Arg-Met-Lys-Lys-Tyr-Met-Ala-Arg-Arg-Lys-Trp-Gln-Lys-Thr-Gly-His-Ala-Val | (I) |
| Lys-Lys-Tyr-Met-Ala-Arg-Arg-Lys-Trp-Gln-Lys-Thr-Gly-His-Ala-Val | (II) |
| Arg,Arg-Lys-Trp-Gln | (III) |
| Lys-Lys-Tyr-Met-Ala-Arg-Arg-Lys-Trp-Gln | (IV) |
| Arg-Met-Lys-Lys-Tyr-Met-Ala-Arg-Arg-Lys-Trp-Gln | (V) |
| Arg-Arg-Lys-Ala-Gln-Lys-Thr-Gly-His-Ala-Val | (VI) |
| Lys-Lys-Tyr-Met-Ala | (VII) |
| Lys-Arg-Lys-Trp-Gln-Lys-Thr-Gly-His-Ala-Val-Ile-Gly-Arg-Leu | (VIII) |
| Arg-Arg-Lys-Trp-Ala-Lys-Thr-Gly-His-Ala-Val | (IX) |
| Ala-Lys-Lys-Leu-Ser-Lys-Asp-Arg-Met-Lys-Lys-Tyr-Met-Ala | (X) |

The polypeptides were purified by reversed-phase HPLC using a Rainin Dynamax® C-8 column developed with a gradient of acetonitrile in 0.1% trifluoroacetic acid. The eluate was monitored by UV absorbance at 215 nm. Each isolated UV peak was monitored for the presence of the desired polypeptide by fast-atom bombardment mass spectrometry [Biemann, Int. J. Mass Spectrom. Ion Phy. 45:183 (1982)].

The structures of the isolated polypeptides were confirmed by Edman degradation [Hewick et al., J. Biol. Chem. 256:7990 (1981)] and by amino acid analysis [HP Amino Quant System, Publication No. 12-5954-8908, Hewlett-Packard GmbH, Waldroun, FGR], using an Applied Biosystems Gas Phase Sequenator (Model 470A) and a Hewlett-Packard Aminoquant System, respectively. All polypeptide concentrations were calculated from the amino acid analysis data.

For convenience, the foregoing polypeptides will be referred to below by the parenthetical Roman numerals following each one. Within the amino acid sequence of each polypeptide shown above, the position of the Arg-Arg-Lys-Trp-Gln subsequence if present is underlined.

Labeling of Human Recombinant Gamma Interferon

Recombinant human gamma interferon was purified to homogenity from an *E. coil* lysate as described in U.S. Pat. No. 4,751,078, although such interferon is available commercially from sources such as Genzyme Corp., Boston, Mass. The amino acid sequence of the interferon used corresponds to the sequence of residues 4-141 of the interferon disclosed by Gray et al. [Nature 295:503 (1982)].

The interferon was labeled with iodine-125, essentially as described by Bolton et al. [Biochem. J. 133:529 (1973)], using $^{125}$I-Bolton-Hunter reagent from New England Nuclear, Boston, Mass. Briefly, 2 mCi (2,000 Ci/mmole) of Bolton-Hunter reagent (New England Nuclear, Boston, Mass.) in anhydrous benzene was dried by a gentle stream of nitrogen. Five micrograms of gamma interferon dissolved in 50 µl of 50 mM sodium phosphate buffer, pH 8.0, were added to the reaction vessel. The reaction was allowed to proceed for 2 hours at room temperature, after which unreacted Bolton-Hunter reagent was quenched with 50 µl of 1M glycine in 50 mM sodium phosphate, pH 8.0.

The radioiodinated protein was separated from unreacted labeling reagent by gel filtration in a 10 ml PD-10 Sephadex G-25® column (Pharmacia LKB Biotechnology, Piscataway, N.J.) equilibrated with 0.05M sodium phosphate buffer, pH 7.4, containing 0.25% gelatin. The labeled interferon retained full antiviral activity ($6 \times 10^6$ units/mg; determined by the method of Rubinstein et al., supra) and had a specific radioactivity of 2400 Ci/mmole, as determined by self-displacement analysis as described by Calvo et al., Biochem. J. 212:259 (1983).

Inhibition of the Binding of $^{125}$I-Recombinant Human Gamma Interferon to Daudi Cells Daudi cells are a well-characterized B lymphoblast cell line derived from a Burkitt lymphoma patient which are available from the American Type Culture Collection under Accession No. ATCC CCL 213.

The receptor assay employed a standard mixture of $6 \times 10^5$ Daudi cells in 1 ml of binding medium (RPMI 1640 medium, 10% fetal bovine serum, 0.02% sodium azide) containing 200,000 cpm of the labeled interferon. Controls additionally contained 1 µg of unlabeled interferon to determine nonspecific binding. Assays were carried out by adding 0.1 ml aliquots of binding medium with or without varying amounts of a potentially inhibitory polypeptide or protein to the standard mixtures, and incubating the combined mixtures for 2 hours at 4° C.

Following the incubation, the cells were pelleted by centrifugation at 13,000× g for 30 seconds at 4° C, and the supernatants were discarded. The cells were resuspended in 0.2 ml of fresh binding medium without labeled interferon at 4° C., after which the cells were centrifuged at 13,000× g for 2 minutes through a layer of dibutyl phthalate and dioctyl phthalate [0.2 ml of a 1:1 (vol/vol) mixture] to remove residual labeled interferon that was not specifically bound. Inhibition constants (Ki) were calculated according to the method of Cheng et al. [Biochem. Pharmacol. 22:3099 (1973)], in which $$Ki = \frac{IC_{50}}{1 + \frac{[L]}{Kd}}$$

where [L] is the ligand concentration and $IC_{50}$ is the concentration of inhibitor required to decrease binding by 50%.

The binding of $^{125}$I-recombinant human gamma interferon to the Daudi cells at 4° C. was saturable and exhibited equilibrium binding characteristics consistent with a single class of high affinity receptors. The equilibrium dissociation constant (Kd) and the total receptor concentration ($B_{max}$) as defined by Scatchard [Ann. N.Y. Acad. Sci. 51:660 (1949)] were as follows:

$Kd = 7.7 \times 10^{-11}$ M $B_{max} = 4.1 \times 10^{-12}$ M

The number of receptors per cell estimated from the $B_{max}$ was 3,799 receptors per cell.

Scatchard analysis of equilibrium binding of the labeled interferon in the presence of a 5 µM concentration of polypeptide I (see above) showed a marked increase in Kd, while the $B_{max}$ remained essentially unaffected. These results were consistent with a competitive type of inhibition.

Figure 1:
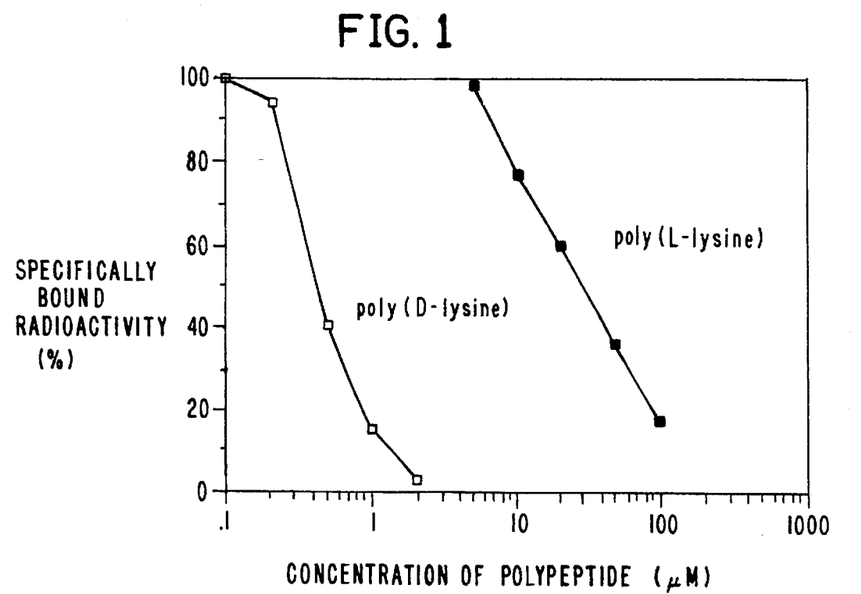
Figure 2:
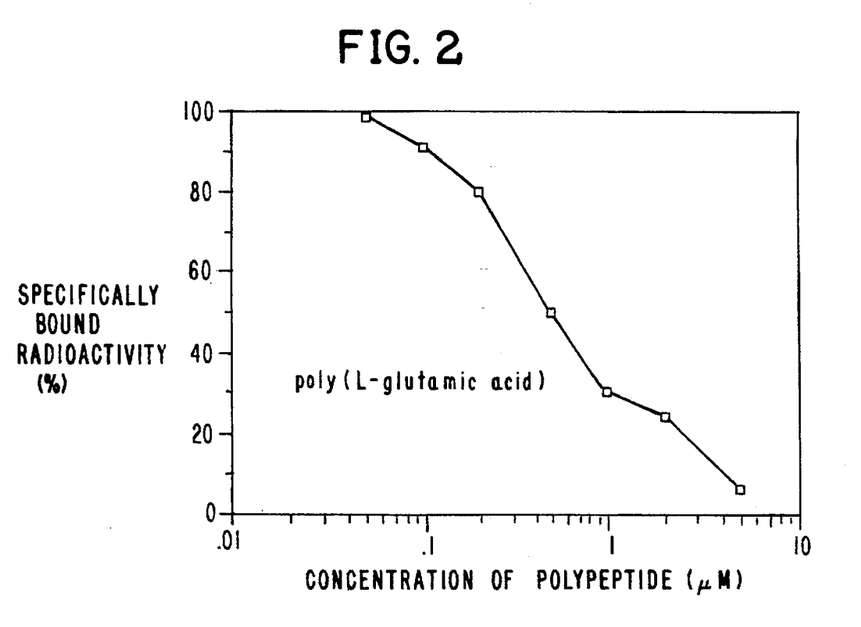
Figure 3:
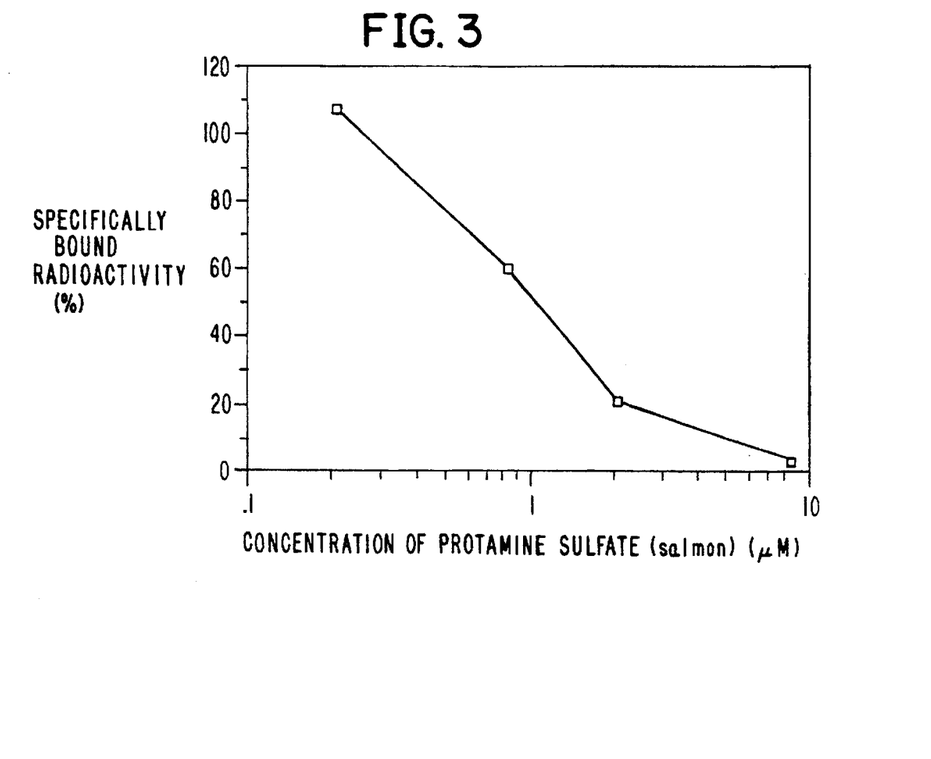
Figure 4:
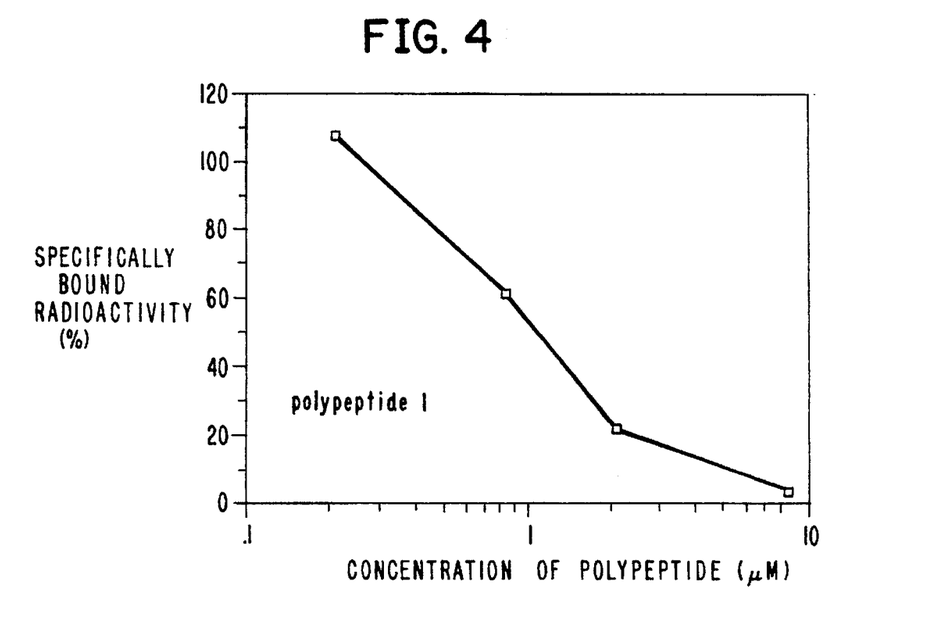

Some of the results obtained are shown graphically in FIGS. 1-4. There, it can be seen that both poly(D-lysine) and poly(L-lysine) were both strong competitive inhibitors of the binding of the labeled interferon (FIG. 1). The Ki values for poly(D-lysine) and poly(L-lysine) were 0.19 and 11 µM, respectively. Similar strong inhibition was shown by poly (L-glutamic acid) (FIG. 2) and by protamine sulfate (FIG. 3), the Ki values of which were found to be 0.29 and 1.1 µM, respectively. FIG. 4 shows similar strong binding inhibition by polypeptide I.

The Ki values for a number of synthetic polypeptides of the invention, all of which contain the Arg-Arg-Lys-Trp-Gln subsequence, are shown in Table 1.

TABLE 1

Inhibition of the Binding of $^{125}$I-Recombinant Human Gamma Interferon to Daudi Cells by Synthetic Polypeptides

| Polypeptide* | Ki(µM) |
| --- | --- |
| I | 3.1 |
| II | 4.0 |
| III | 9.6 |
| IV | 10 |
| V | 16 |

*Amino acid sequences of the polypeptides are shown above.

The data of Table 1 show that an Arg-Arg-Lys-Trp-Gln pentapeptide itself (III) is a highly effective inhibitor of the binding of the labeled interferon to Daudi cells. Whether other amino acid residues are attached to the amino terminus (IV or V) or to both the amino and carboxyl termini (I and II) of this pentapeptide has little effect upon the observed Ki.

To further demonstrate the importance of the pentapeptide subsequence of the polypeptides of the invention, other polypeptides were synthesized in which the subsequence was not present or was modified. These polypeptides were tested in the same manner, with the results shown in Table 2.

TABLE 2

Effect of Deletion or Modification of the Pentapeptide Subsequence on Ki

| Polypeptide* | Ki(µM) |
| --- | --- |
| VI | 43 |
| VII | >53 |
| VIII | 180 |
| IX | >180 |
| X | 404 |

*Amino acid sequences of the polypeptides are shown above.

The data of Table 2 show that replacement of the tryptophan of the pentapeptide with alanine (VI), the amino-terminal arginine with lysine (VIII) or the glutamine with alanine (IX) produced markedly higher Ki values. Similar results were observed when the pentapeptide subsequence was entirely absent from the polypeptides (VII and X).

Inhibition of Biological Effects of Gamma Interferon

To demonstrate that the inhibition of the binding of gamma interferon to its cellular receptors by the polypeptides and proteins of the invention produces biological effects, the actions of two representative polypeptides were observed in two interferon-responsive biological systems.

Reagents and Cells

Stock cultures of human diploid foreskin cells were grown and maintained in roller bottles (850 $cm^2$) in Minimal Essential Medium (MEM) with Earle's salts supplemented with 10% heat-inactivated fetal calf serum (Medium A). The cultures were routinely passaged each week by trypsinization of the monolayers with a 1:2 subculture of the cells. For use in antiviral assays, the cells were trypsinized from the stock roller bottles into Medium A to form a suspension with $3.5\times10^5$ cells/ml.

Encephalomyocarditis (EMC) virus stock (ATCC VR-129) prepared from infected Vero cells was used to infect the foreskin cells. Supernatant fluids from the infected Vero cells were harvested, titered, dispensed in 1.0 ml aliquots and stored at −80° C. until used for assay.

Recombinant human gamma interferon D having a specific activity of about $4\times10^6$ units/mg was prepared from transformed *E. coil* using standard methods.

COLO-205 cells (ATCC CRL 1583) derived from a human adenocarcinoma were used to measure the induction by the interferon of class II major histocompatibility antigens (HLA-DR). The presence of the antigens on the cells was detected by Enzyme-Linked Immunosorbent Assay (ELISA) using a mouse monoclonal anti-HLA-DR antibody (Becton-Dickinson Catalog No. 7360) in conjunction with a peroxidate-labeled goat anti-mouse IgG. Color produced using 2,2'-Azino-bis(3-Ethylbenzthiazoline-6-Sulfonic Acid) (ABTS; Kirkegaard & Perry Labs., Inc., Gaithersburg, Md.) was measured spectrophotometrically at 405 nm.

Inhibition of Antiviral Activity

Control Medium A, various dilutions in Medium A of recombinant human gamma Interferon D in the presence of a fixed concentration of polypeptide No. I, or various dilutions of Medium A of polypeptide No. III in the presence of a fixed concentration of the interferon were pipetted in 0.1 ml total volumes into the wells of 96-well flat bottom microtiter plates.

Aliquots of a suspension of human diploid foreskin cells (0.1 ml, $3.5 \times 10^5$ cells/ml) in Medium A were pipetted into the wells of the microtiter plates, and the plates were incubated for 4 hours in a 37° C., 5% $CO_2$ incubator. Following this incubation, the supernatant fluids were removed and the cells were washed with Hank's medium and then incubated for 2 hours at 37° C. in Eagle's MEM with 2% fetal calf serum.

EMC virus was added in 0.05 ml of Medium A at a concentration of 0.015 pfu/cell, and the cells were further incubated at 37° C. (typically about 16–18 hours) until maximum cytopathic effect (CPE) was observed in wells containing only virus and cells. The medium was aspirated and discarded from all wells at this point.

A 0.025–0.05 aliquot of a solution of crystal violet stain (Sigma Chemical Co., St. Louis, Mo.; 0.485% in an aqueous solution containing 3.2% formaldehyde and 32.3% 95% ethanol) was added to each well, and the plates were allowed to stand for 30 minutes for color development. The stain solution was removed and the wells were washed at least three times with distilled water, after which the plates were scored for CPE with the aid of a fluorescent light viewer.

CPE was graded semi-quantitatively on a scale of 0 to 4, with grade O CPE corresponding to a complete absence of cell lysis as measured by cell staining with crystal violet and grade 4 CPE corresponding to total cell lysis and lack of staining.

Figure 5:
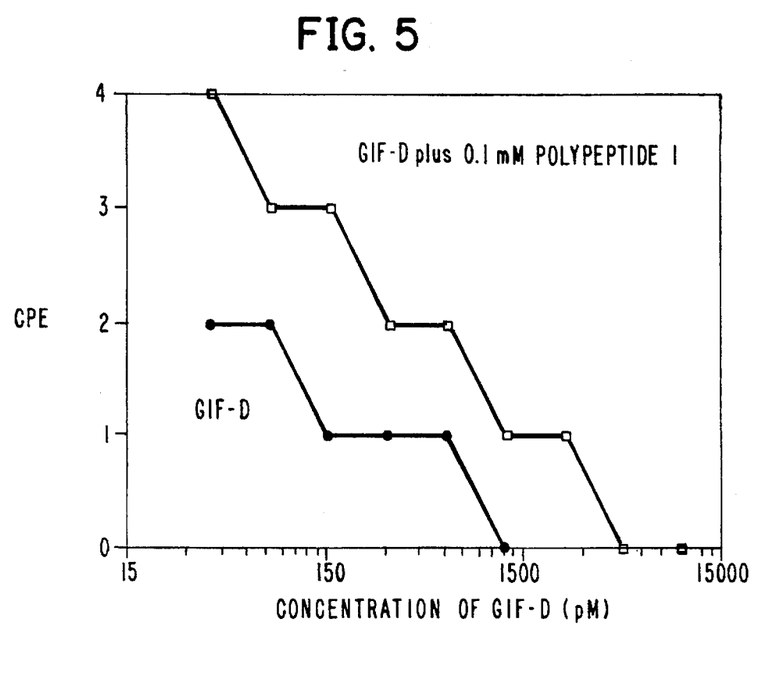
FIG. 5 is a graphical representation of the inhibition by the polypeptide described in the legend to FIG. 4 of the antiviral effects of recombinant human gamma interferon D on human diploid foreskin cells challenged with encephalomyocarditis virus. Cytopathic effects (CPE) are shown as a function of interferon concentration, with (upper curve) and without (lower curve) the polypeptide at a 0.1 mM concentration.

The results of such an assay are shown in FIG. 5, where it can be seen from the lower curve that a concentration of interferon alone of 1,200 pM produced complete cell protection; a concentration of 30 pM produced a grade 2 CPE. In the presence of 0.1 mM polypeptide I (upper curve), however, the same interferon levels provided substantially less protection to the cells. With the polypeptide, interferon concentrations of 1,200 and 30 pM produced CPEs of grades 1 and 4, respectively.

Figure 6:
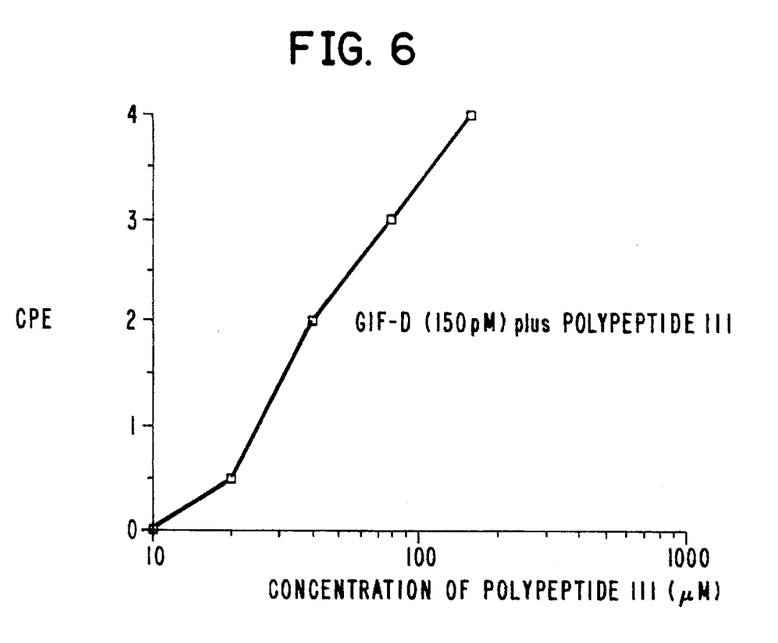
FIG. 6 is a graphical representation of the inhibition by a synthetic polypeptide having the amino acid sequence Arg-Arg-Lys-Trp-Gln of the antiviral effects of recombinant human gamma interferon D on human diploid foreskin cells challenged with encephalomyocarditis virus. Cytopathic effects (CPE) are shown as a function of polypeptide concentration in the presence of a constant 150 pM interferon concentration.

Results of an assay in which a constant 150 pM concentration of interferon was used with varying amounts of polypeptide III are shown in FIG. 6. There, it can be seen that the interferon in the presence of only 10 μM polypeptide provided complete protection of the cells. As the polypeptide concentration was increased from 10 to 105 μM, however, CPE steadily increased, reaching grade 4 at the highest concentration.

Inhibition of HLA-DR Induction

Bio-ELISA assay for HLA-DR induction by gamma interferon was carried out essentially as described by Gibson et al. [J. Immunol. Meth. 125:103 (1989)]. Briefly, COLO-205 cells were grown to confluence in T-75 flasks in RPMI 1640 medium containing 10% fetal calf serum (culture medium). The cells were trypsinized and seeded in 96-well tissue culture plates at a density of $5 \times 10^4$ cells per well in 0.1 ml of culture medium. The cells were allowed to attach to the wells by overnight incubation at 37° C. in a 5% $CO_2$ incubator.

Control culture medium, various dilutions in culture medium of recombinant human gamma interferon D in the presence of a fixed concentration of polypeptide No. III, or various dilutions in culture medium of polypeptide No. III in the presence of a fixed concentration of the interferon were added in a 0.1 ml volume to the wells and incubated for one hour at 37° C.

Following this incubation, the medium was removed from each well and the wells were washed three times with culture medium. Aliquots (0.1 ml) of culture medium were added to the wells, and the plates were incubated for 18 hours at 37° C. to allow for induction of HLA-DR antigen expression by interferon bound to the cells.

The wells were washed with 0.2 ml of phosphate buffered saline (PBS; 0.02M sodium phosphate, 0.15M NaCl, pH 7.4) and then fixed for two minutes with ice-cold anhydrous ethyl alcohol. The alcohol was removed, and the wells were washed once with 0.2 ml of PBS. Fifty microliters of a 1:50 dilution of the mouse monoclonal anti-HLA-DR antibody in PBS containing 0.5% bovine serum albumin were then added to each well, and the plates were incubated for one hour at room temperature.

Excess reagent was removed by washing the wells three times with 0.2 ml of PBS, after which 0.1 ml of a 1:5,000 dilution of peroxidase-labeled goat anti-mouse IgG was added to each well. The plates were incubated for one hour at room temperature. After washing each well three times with PBS as before, color was developed by the addition of ABTS for 5–10 minutes at room temperature. Absorbance was measured at 405 nm using an ELISA plate reader.

Figure 7:
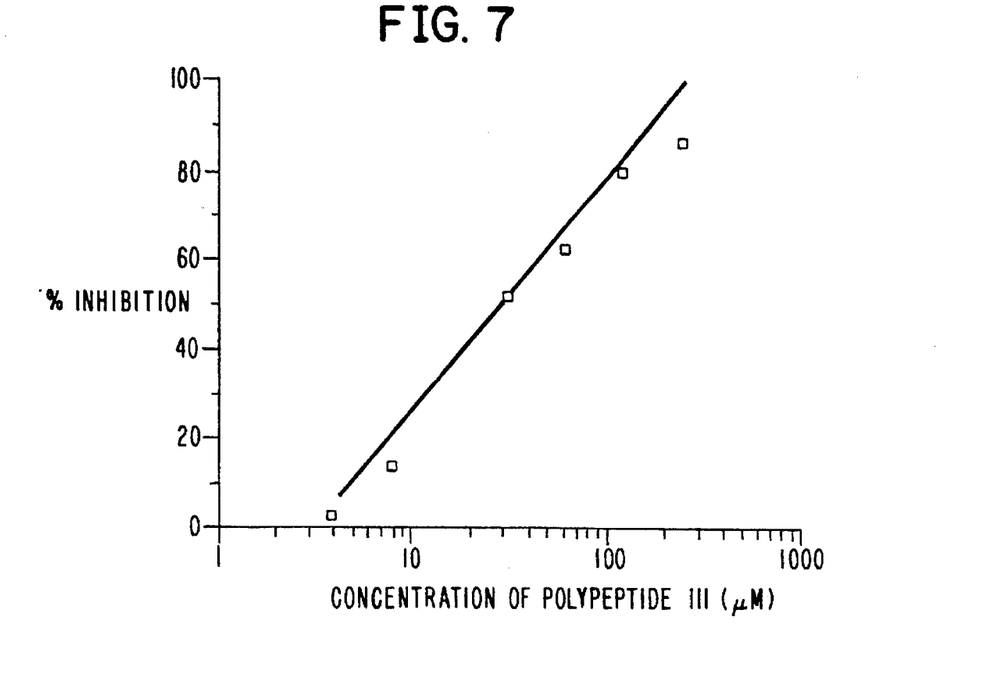
FIG. 7 is a graphical representation of the inhibition by the polypeptide described in the legend to FIG. 6 of the induction of class II major histocompatibility antigens on COLO-205 cells by recombinant human gamma interferon D. Percent inhibition is shown as a function of polypeptide concentration in the presence of a constant 63 pM concentration of interferon.

Results of an assay to measure inhibition of gamma interferon-induced HLA-DR expression in COLO-205 cells by polypeptide No. III are shown in FIG. 7. There, it can be seen that increasing concentrations of the polypeptide from 4 to 115 μM produced progressively greater inhibition of antigen induction by a constant 63 pM concentration of interferon.

Figure 8:
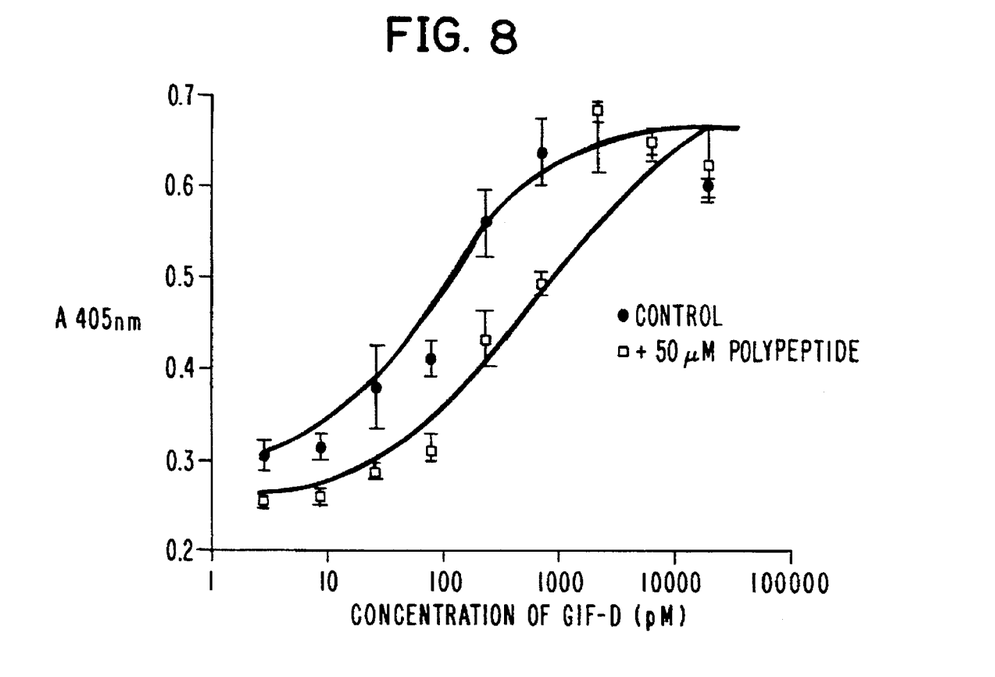
FIG. 8 is a graphical representation of the effect of the polypeptide described in the legend to FIG. 6 on the induction of class II major histocompatibility antigens on COLO-205 cells by recombinant human gamma interferon D. ELISA antigen measurement (absorbance at 405 nm) is shown as a function of interferon concentration with (lower curve) and without (upper curve) a 50 µM concentration of the polypeptide.

FIG. 8 shows a similar inhibition by polypeptide No. III. The data of FIG. 8 were produced by treating the cells with varying concentrations of recombinant human gamma interferon D alone (upper curve) or in the presence of 50 μM polypeptide No. III. The effect of the polypeptide was to shift the interferon dose-response curve to the right, with about a ten-fold higher interferon concentration needed to produce maximal induction.

Many modifications and variations of this invention may be made without departing from its spirit and scope, as will become apparent to those skilled in the art. The specific embodiments described herein are offered by way of example only, and the invention is to be limited only by the terms of the claims.

What is claimed is:

1. A polypeptide selected from the group consisting of
Arg-Arg-Lys-Trp-Gln,
Lys-Lys-Tyr-Met-Ala-Arg-Arg-Lys-Trp-Gln,
Arg-Met-Lys-Lys-Tyr-Met-Ala-Arg-Arg-Lys-Trp-Gln, and
Lys-Lys-Tyr-Met-Ala-Arg-Arg-Lys-Trp-Gln-Lys-Thr-Gly-His-Ala-Val.

2. A method of inhibiting the binding of gamma interferon to a gamma interferon receptor, comprising contacting invitro cells bearing receptors for gamma interferon with an effective amount of a polypeptide selected from the group consisting of:
Arg-Arg-Lys-Trp-Gln,
Lys-Lys-Tyr-Met-Ala-Arg-Arg-Lys-Trp-Gln,
Arg-Met-Lys-Lys-Tyr-Met-Ala-Arg-Arg-Lys-Trp-Gln,
Lys-Lys-Tyr-Met-Ala-Arg-Arg-Lys-Trp-Gln-Lys-Thr-Gly-His-Ala-Val, and
Ala-Lys-Lys-Leu-Ser-Lys-Asp-Arg-Met-Lys-Lys-Tyr-Met-Ala-Arg-Arg-Lys-Trp-Gln-Lys-Thr-Gly-His-Ala-Val.

3. A method for inhibiting antiviral effects of gamma interferon, comprising contacting invitro cells capable of responding to gamma interferon by producing an antiviral response with an effective amount of a polypeptide selected from the group consisting of:

Arg-Arg-Lys-Trp-Gln,

Lys-Lys-Tyr-Met-Ala-Arg-Arg-Lys-Trp-Gln,

Arg-Met-Lys-Lys-Tyr-Met-Ala-Arg-Arg-Lys-Trp-Gln,

Lys-Lys-Tyr-Met-Ala-Arg-Arg-Lys-Trp-Gln-Lys-Thr-Gly-His-Ala-Val, and

Ala-Lys-Lys-Leu-Ser-Lys-Asp-Arg-Met-Lys-Lys-Tyr-Met-Ala-Arg-Arg-Lys-Trp